United States Patent
Wetsel et al.

(10) Patent No.: US 8,343,481 B2
(45) Date of Patent: Jan. 1, 2013

(54) METHOD OF PREPARING LUNG ALVEOLAR EPITHELIAL TYPE II CELLS DERIVED FROM EMBRYONIC STEM CELLS

(75) Inventors: Rick A. Wetsel, Houston, TX (US); Dachun Wang, Houston, TX (US)

(73) Assignee: Board of Regents of The University of Texas System, Austin, TX (US)

( * ) Notice: Subject to any disclaimer, the term of this patent is extended or adjusted under 35 U.S.C. 154(b) by 251 days.

(21) Appl. No.: 12/527,969

(22) PCT Filed: Feb. 21, 2008

(86) PCT No.: PCT/US2008/054553
§ 371 (c)(1),
(2), (4) Date: Sep. 28, 2009

(87) PCT Pub. No.: WO2008/103810
PCT Pub. Date: Aug. 28, 2008

(65) Prior Publication Data
US 2010/0021443 A1    Jan. 28, 2010

Related U.S. Application Data

(60) Provisional application No. 60/890,958, filed on Feb. 21, 2007.

(51) Int. Cl.
*A61K 35/12* (2006.01)
*C12Q 1/02* (2006.01)
(52) U.S. Cl. .................. 424/93.21; 435/29; 424/93.7

(58) Field of Classification Search ................ None
See application file for complete search history.

(56) References Cited

OTHER PUBLICATIONS

Ali et al. (Tissue Engineering. 2002; 8(4): 541-550).*
Xu et al. (Biotech Nature. Oct. 2001; 19: 971-974).*
Brochiero et al. (Am J Physiol lung Cell Mol Physiol. 2004; 287: :382-L392).*
Fehrenbach (Respiratory Research. 2001; 2:33-46).*
Perl et al (PNAS. Aug. 6, 2002; 99(16): 10482-10487).*
Novak et al. (Genesis. 2000; 28:147-155).*

* cited by examiner

*Primary Examiner* — Scott Long
(74) *Attorney, Agent, or Firm* — Conley Rose, P.C.

(57) ABSTRACT

A method of preparing a population of in vitro cultured cells of alveolar epithelial type II (ATII) cell lineage derived from at least one embryonic stem cell is disclosed which comprises (a) culturing said at least one embryonic stem cell in vitro in a medium comprising MATRIGEL®, to produce differentiated cells without formation of an embryonic body, wherein at least some of the differentiated cells are of ATII cell phenotype; (b) identifying the differentiated cells of ATII cell phenotype by detecting expression of at least one biomarker of ATII cells; (c) isolating the differentiated cells having ATII cell phenotype; and (d) cloning the isolated cells to produce a population of cells having ATII cell phenotype. The resulting cells are preferably >99% pure ATII phenotype lineage and are potentially useful therapeutically for treating lung injury and disease.

15 Claims, 8 Drawing Sheets

SEQUENCE LISTING

```
<160> NUMBER OF SEQ ID NOS: 8

<210> SEQ ID NO 1
<211> LENGTH: 24
<212> TYPE: DNA
<213> ORGANISM: Artificial
<220> FEATURE:
<223> OTHER INFORMATION: Synthetic sequence

<400> SEQUENCE: 1
tggtcctcat cgtcgtggtg attg                                              24

<210> SEQ ID NO 2
<211> LENGTH: 26
<212> TYPE: DNA
<213> ORGANISM: Artificial
<220> FEATURE:
<223> OTHER INFORMATION: Synthetic sequence

<400> SEQUENCE: 2
cctgcagaga gcattccatc tggaag                                            26

<210> SEQ ID NO 3
<211> LENGTH: 30
<212> TYPE: DNA
<213> ORGANISM: Artificial
<220> FEATURE:
<223> OTHER INFORMATION: Synthetic sequence

<400> SEQUENCE: 3
ggagggattt ggggaattat ttgagaaagc                                        30

<210> SEQ ID NO 4
<211> LENGTH: 30
<212> TYPE: DNA
<213> ORGANISM: Artificial
<220> FEATURE:
<223> OTHER INFORMATION: Synthetic sequence

<400> SEQUENCE: 4
ctatattcat cataggaaac accaaagatg                                        30

<210> SEQ ID NO 5
<211> LENGTH: 25
<212> TYPE: DNA
<213> ORGANISM: Artificial
<220> FEATURE:
<223> OTHER INFORMATION: Synthetic sequence
```

```
<400> SEQUENCE: 5
tgacactcac gatgaaatcc tggag                                          25

<210> SEQ ID NO 6
<211> LENGTH: 26
<212> TYPE: DNA
<213> ORGANISM: Artificial
<220> FEATURE:
<223> OTHER INFORMATION: Synthetic sequence

<400> SEQUENCE: 6
ccttgagtac ccttctccac gtaatc                                         26

<210> SEQ ID NO 7
<211> LENGTH: 21
<212> TYPE: DNA
<213> ORGANISM: Artificial
<220> FEATURE:
<223> OTHER INFORMATION: Synthetic sequence

<400> SEQUENCE: 7
taacgaacga gactctggca t                                              21

<210> SEQ ID NO 8
<211> LENGTH: 22
<212> TYPE: DNA
<213> ORGANISM: Artificial
<220> FEATURE:
<223> OTHER INFORMATION: Synthetic sequence

<400> SEQUENCE: 8
cggacatcta agggcatcac ag                                             22
```

METHOD OF PREPARING LUNG ALVEOLAR EPITHELIAL TYPE II CELLS DERIVED FROM EMBRYONIC STEM CELLS

STATEMENT REGARDING FEDERALLY SPONSORED RESEARCH OR DEVELOPMENT

This invention was made with government support under Grant No. AI25011 awarded by the National Institutes of Health. The government has certain rights in the invention.

BACKGROUND OF THE INVENTION

1. Field of the Invention

The present invention generally relates to the differentiation of embryonic stem cells in tissue culture into specific cell lineages, particularly cells of alveolar epithelial type II phenotype. The invention also relates to the therapeutic use of such differentiated cells in vivo.

2. Description of Related Art

The alveolar epithelium covers more than 99% of the internal surface area of the lung and is composed of two major cell types, the alveolar type I (ATI) cell and the alveolar type II (ATII) cell. ATI cells are large flat cells through which exchange of $CO_2/O_2$ takes place. They cover about 95% of the alveolar surface and comprise approximately 40% of the alveolar epithelium and 8% of the peripheral lung cells. In contrast, ATII cells are small, cuboidal cells, which cover about 5% of the alveolar surface and comprise 60% of the alveolar epithelium and 15% of the peripheral lung cells. They are characterized by the unique ability to synthesize and secrete surfactant protein C (SPC) and by the distinct morphological appearance of inclusion bodies, known as lamellar bodies. Important functions of ATII cells are: (i) to synthesize, store, and secrete surfactant, which reduces surface tension preventing collapse of the alveolus, (ii) to transportions from the alveolar fluid into the interstitium, thereby minimizing alveolar fluid and maximizing gas exchange, (iii) to serve as progenitor cells for alveolar type I cells, which is particularly important during re-epithelialization of the alveolus after lung injury, and (iv) to provide pulmonary host defense by synthesizing and secreting several complement proteins including C3 and C5 (1-3) as well as numerous cytokines and interleukins that modulate lymphocyte, macrophage and neutrophil functions (4). Severe pulmonary diseases can be caused by deficiencies or genetic mutations in proteins synthesized by AII cells that are important in maintaining normal lung homeostasis. For example, cystic fibrosis is caused by mutations in the transmembrane conductance receptor (CFTR) (5). CFTR is an important regulator of $Cl^-$ and liquid transport in the lung (6-9), and is functionally expressed by human ATII cells, strongly suggesting a critical role for CFTR in regulating ion and fluid transport in the lung alveolus (8). In addition, ATII cells synthesis and secrete the serine protease inhibitor, alpha-1 antitrypsin ($\alpha$-1AT), which also plays a key role in alveolar homeostasis by regulating protease imbalance and adjusting fluid clearance (10, 11), the importance of which is supported by the association of $\alpha$-1AT deficiency with the development of pulmonary emphysema (12).

Embryonic stem (ES) cells isolated from the inner cell mass of blastocyst-stage embryos are undifferentiated, pluripotent cells (13, 14), which can be induced to differentiate in vitro into a wide range of different cell types (15-23). The potential clinical use of ES cells to regenerate or repair damaged tissue has fueled a tremendous amount of research activity to develop methods that promote the differentiation of ES cells into specific cell lineages. Because of its numerous important functions, including its ability to proliferate and differentiate into the easily damaged ATI cell, human ES cell-derived ATII (hES-ATII) cells are promising as a source of cells that could be used therapeutically to treat distal lung injury as well as pulmonary genetic disorders. Recently published data demonstrated that ES cells can be differentiated into ATII cells via embryonic body (EB) formation (24, 25) or co-culture of EBs with pulmonary mesenchyme (26). However, these procedures were not efficient, generating only a very small percentage of ES cell-derived ATII cells (27). A mixed population of cell derivatives, as those generated in these reports, will not be suitable for transplantation into the lung. In addition, the pluripotent cells in the differentiating cultures carry a significant risk of producing teratomas after transplantation in vivo. Therefore, a major prerequisite for using ATII cells therapeutically is to achieve a pure population of hES-ATII cells. Selection strategies such as those employing protein markers or drug-resistance genes under the control of cell-specific promoters may be highly effective in producing a pure culture of ES cell-derived donor cells (28).

SUMMARY

Embodiments of the invention seek to overcome certain drawbacks inherent in the prior art by providing methods of preparing a population of in vitro cultured cells of alveolar epithelial type II (ATII) cell lineage derived from at least one embryonic stem cell. In accordance with certain embodiments, a method comprises (a) culturing the at least one embryonic stem cell in vitro in a medium comprising MATRIGEL® (a gelatinous protein mixture secreted by Engelbreth-Holm-Swarm (EHS) mouse sarcoma cells), to produce differentiated cells without formation of an embryonic body, wherein at least some of the differentiated cells are of ATII cell phenotype; (b) identifying the differentiated cells of ATII cell phenotype by detecting expression of at least one biomarker of ATII cells; (c) isolating the differentiated cells having ATII cell phenotype; and (d) cloning the isolated cells to produce a population of cells having ATII cell phenotype.

In some embodiments the at least one biomarker comprises surfactant protein C. In some embodiments the at least one biomarker comprises cystic fibrosis transmembrane conductance receptor. In some embodiments the at least one biomarker comprises $\alpha$-1-antitrypsin. In some embodiments the at least one biomarker comprises complement protein C3 or C5, or both C3 and C5.

In some embodiments, at least one embryonic stem cell comprises a transgene operably linked to a cell-specific promoter. For example, the predetermined transgene may comprise a drug resistance gene that, when expressed, is capable of imparting resistance to the drug in the stem cell or progeny thereof.

In some embodiments, in the above-described step (c), isolating the differentiated cells having the ATII cell phenotype comprises selecting a purified population of differentiated cells wherein at least 99% of the cells have ATII cell phenotype.

In some embodiments, in the above-described step (d), cloning the isolated cells to produce a population of cells having ATII cell phenotype comprises producing a population of more than $10^6$ cells within 15 days of differentiation, wherein at least 99% of the population have ATII phenotype.

In accordance with certain other embodiments of the invention, an in vivo method of repairing injured or diseased alveolar epithelial tissue in the lung of a mammal is provided which comprises transplanting into the lung, at a site comprising injured or diseased alveolar epithelial tissue, a population of differentiated embryonic stem cells, or progeny thereof, at least 99% of which have ATII phenotype. The population of cells with ATII phenotype is prepared as described above, and, after transplantation, is effective to repair at least a portion of the injured or diseased alveolar epithelial tissue at the site. In some embodiments, the at least one differentiated embryonic stem cell, or progeny thereof, comprises a transgene operably linked to a cell-specific promoter, wherein the transgene encodes a therapeutic gene product.

Also provided in accordance with certain embodiments of the invention is an in vivo method of treating a genetic disease affecting alveolar epithelial tissue in the lung of a mammal. This method comprises transplanting into the lung, at a site comprising alveolar epithelial tissue detrimentally affected by the genetic disease, a population of differentiated embryonic stem cells, or progeny thereof, at least 99% of which have ATII phenotype, wherein the population of cells is prepared by an above-described method. The transgene encodes a gene product that ameliorates the genetic disease or its detrimental effects in the alveolar epithelial tissue. In some embodiments the a differentiated embryonic stem cell, or its progeny, comprise a transgene encoding a therapeutic gene product is operably linked to a cell-specific promoter. Thus, embodiments described herein comprise a combination of features and advantages intended to address various shortcomings of the prior art. The various characteristics described above, as well as other features, will be readily apparent to those skilled in the art upon reading the following detailed description of the preferred embodiments, and by referring to the accompanying drawings.

DETAILED DESCRIPTION

An aim of the study leading up to the present invention was to achieve a pure population of hES-ATII (hES-ATII) cells as a promising source of cells for use therapeutically to treat distal lung diseases, lung injuries, and genetic diseases that affect the lung. This is believed to be the first report of a successful effort to generate a pure culture of hES-ATII cells suitable for transplantation.

Overview

A reliable transfection and culture procedure has been developed which facilitates the differentiation of human ES (hES) cells into an essentially pure (>99%) population of ATII cells. Purity as well as biological features and morphological characteristics of normal ATII cells were demonstrated for the hES-ATII cells by RT-PCR, flow cytometric analysis, immunofluorescence staining, and by ultrastructural examination. Moreover, the hES-ATII cells were shown to express genes and synthesize proteins well known for their importance in lung function, inflammation, host-defense and pulmonary genetic disorders. Collectively, these data document for the first time the successful generation of a pure population of hES cell-derived ATII cells that are more suitable that previous hES-derived ATII cells for transplantation into the lung for potential repair of damaged tissue or for therapeutic treatment of genetic diseases.

EXPERIMENTAL STUDIES

Methods

Human Surfactant Protein C Promoter-Neomycin Vector.

Figure 1:
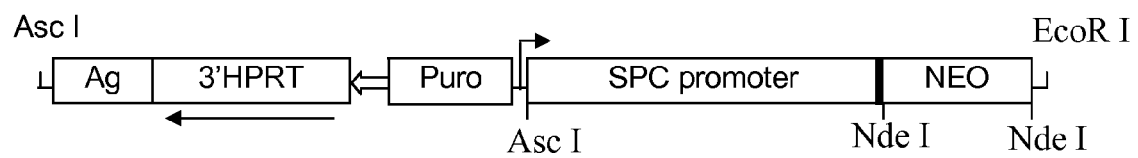
FIG. 1 is a schematic drawing showing the structure of the SPC promoter-NEO transgene 3' HPRT vector. A 3.8 kb human genomic DNA fragment containing the SPC promoter and 170 bp of non-coding sequence of exon 1 was cloned into the 3' hprt targeting vector, containing the puromycin resistance gene. The Neo$^r$ gene was added downstream of the SPC promoter. The EcoR I site located between the Agouti and Neo$^r$ gene was used to linearize the plasmid before transfection.

A 3.8 kb fragment of human genomic DNA containing the human SPC promoter and 170 bp of non-coding sequence of exon 1 (34) was cloned into the Asc I site of the 3'-hprt insertion targeting vector (35) (a gift from Dr. Allan Bradley, The Wellcome Trust Sanger Institute, UK). The Neo$^r$ cDNA-poly A fragment was sub-cloned into an engineered Nde I restriction site downstream of the SPC promoter. The resulting vector (3'-hprt-SPCP.NEO) is depicted in FIG. 1, and was linearized by EcoRI before transfection.

Transfection and Selection of Human Embryonic Stem Cells.

The NIH approved human embryonic stem (hES) cell line, H9.2 (passages 45-65) (WiCell, Madison, Wis.), was used throughout this study. Undifferentiated hES cells were cultured on mitotically inactivated mouse embryonic fibroblasts (MEFs) in 6-well plates with hES cell culture medium, containing 80% Dulbecco's modified Eagle's medium (DMEM)/F12, 20% knockout serum replacement (Gibco Invitrigen), 1% non-essential amino acid, 1 mM L-glutamine (Chemicon), 0.1 mM 2-mercaptoethanol, and 4 ng/ml basic fibroblast growth factor (Gibco Invitrogen). The hES cells from one 6-well plate were re-suspended in 100 µl of supplemented Mouse ES Cell Nucleofector Solution and mixed with 5 ug of the linearized 3'hprt-SPCP.NEO vector and transfected using the cell Nucleofector™ II (Amaxa). The hES cells were then plated on MATRIGEL® coated 10-cm plates with MEFs conditioned hES cell medium (MEF-CM) (36). The 3'-hprt-SPCP.NEO transfected hES cells were selected in the presence of 0.25 µg/ml puromycin (Sigma) for 14 days. Surviving ES clones were examined for the Neor gene by PCR analysis, and a positive clone (SPCP/Neo.74) containing a single copy of the transgene was selected for further analysis.

In Vitro Differentiation and Selection of ES Cell-Derived Alveolar Epithelial Type II Cells.

To induce spontaneous differentiation via EB formation, collagenase IV dissociated hES cells were plated on 6-well ultra low attachment plates in hES cell medium. On day 2, the resultant EBs were collected, washed, and cultured on fresh 6-well ultra low attachment plates with Differentiation Medium (DM), composed of 80% knockout DMEM (Gibco Invitrigen), 20% FBS, 1% non-essential amino acid, 1 mM L-glutamine, penicillin (100 u/ml), and streptomycin (100 µg/ml). On day 6, the EBs were collected and seeded on gelatin-coated 6-well culture plates in DM (15 EBs per well) and allowed to expand. Selection of hES cell derived ATII cells was started on day 6 by adding 20 µg/ml G418 (GIBCO). To promote the differentiation without EB formation, the collagenase IV dissociated hES cells were seeded on MATRIGEL® coated 6-well plates with MEF-CM (day 0). On day 1, the medium was replaced by DM with or without G418 (20 µg/ml).

RT-PCR.

Total RNA was isolated from the hES cultures using RNA Bee™ (Tel-Test, Inc.) following the manufacturer's protocol. The following primer pairs were used in the RT-PCR reactions, employing 0.5 µg total RNA and the OneStep RT-PCR kit (Qiagen): (i) SPC forward (5'-TGG TCC TCA TCG TCG TGG TGA TTG-3') (SEQ ID NO: 1) and SPC reverse (5'-CCT GCA GAG AGC ATT CCA TCT GGA AG-3') (SEQ ID NO: 2), (ii) CFTR forward (5'-GGA GGG ATT TGG GGA ATT ATT TGA GAA AGC-3') (SEQ ID NO: 3), and CFTR reverse(5'-CTA TAT TCA TCA TAG GAA ACA CCA AAG ATG-3') (SEQ ID NO: 4), (iii) α1-AT forward (5'-TGA CAC TCA CGA TGA AAT CCT GGA G-3') (SEQ ID NO: 5) and α1-AT reverse (5'-CCT TGA GTA CCC TTC TCC ACG TAA TC-3') (SEQ ID NO: 6), and (iv) 18S forward (5' TAA CGA ACG AGA CTCTGG CAT 3') (SEQ ID NO: 7) and 18S reverse (5'CGG ACA TCT AAG GGC ATC ACA G 3') (SEQ ID NO: 8).

Immunofluorescence and Flow Cytometry.

Differentiated hES cells were dissociated into single cell suspensions by incubation with 0.25% trypsin for 2 min. The dissociated cells were resuspended (0.3×10$^6$ cells) in 250 µl of Fixation/Permeabilization solution (Cytofix/Cytoperm kit, BD biosciences), kept on ice for 20 min, and washed twice with Perm/Wash™ buffer. After blocking with 10% goat serum in 300 µl Perm/Wash™ buffer for 45 min on ice, the cells were incubated with rabbit anti-human proSPC antibody (1:200 dilution, Chemicon) in the block solution for 45 min on ice. The cells were resuspended in 350 µl of Perm/Wash™ buffer after incubated with goat anti-rabbit IgG conjugated by R-Phycoerythrin (1:300 dilution, Sigma) for 45 min on ice and washed twice, and analyzed by flow cytometry. For immunofluorescent staining, the differentiated hES cells, with or without G418 selection, were dissociated and seeded on poly-D-lysine coated cover slips, cultured for 24 hr and stained with the rabbit anti-human proSPC antibody following the manufacturer's directions. The SPC positive cells were visualized with Alexa Fluor 546 conjugated goat anti-rabbit IgG (1:1000, Molecular Probes) with DAPI counterstaining. The number of SPC positive cells was counted per 500 cells based on the DAPI staining on each slide. This procedure was also used for immunostaining of surfactant protein A (SPA) and surfactant protein B (SPB) using rabbit anti-human SPA and anti-human proSPB (1:1000, Chemicon).

Electron Microscopy.

The G418 selected hESC derived ATII cells and A549 cells were trypsinized and fixed (2 hr) in suspension with 0.1 M sodium cacodylate buffer containing 2.5% glutaraldehyde and then post-fixed in 1% tannic acid (5 min) followed by 1% osmium tetroxide (1 hr) and then aqueous uranyl acetate (1 hr). Samples were subsequently dehydrated in a graded ethanol series, embedded in Araldite resin and ultrathin serial sections (100 nm) were obtained using an ultramicrotome (RMC 7000, RMC, AZ) equipped with a diamond knife. Sections were stained with uranyl acetate and lead citrate before photographing with a JEOL 200CX electron microscope.

ELISA Analysis.

Cultures (4, 9, 11, or 14 days) of differentiating hES cell-derived ATII cells and A549 cells were switched to DMEM with 15% FBS, incubated for 24 hrs, and 100 µl samples of each culture added to 96-well plates, which had been coated with either anti-human C3c or anti-human C5 antibodies (2 µg/ml, Quidel). After incubation at room temperature for 2 hrs, the plates were exhaustively washed, incubated for 2 hrs with the primary goat anti-human C3 and anti-human C5 antibodies (Complement Technology, Inc.), washed, and incubated for 1 hr. with alkaline phosphatase conjugated rabbit anti-goat IgG (Sigma). Samples were developed using the Alkaline Phosphatase Yellow Liquid Substrate System (Sigma).

Results

Derivation and Selection of Alveolar Epithelial Type II (ATII) Cells from hES Cell Lines.

Figure 2:
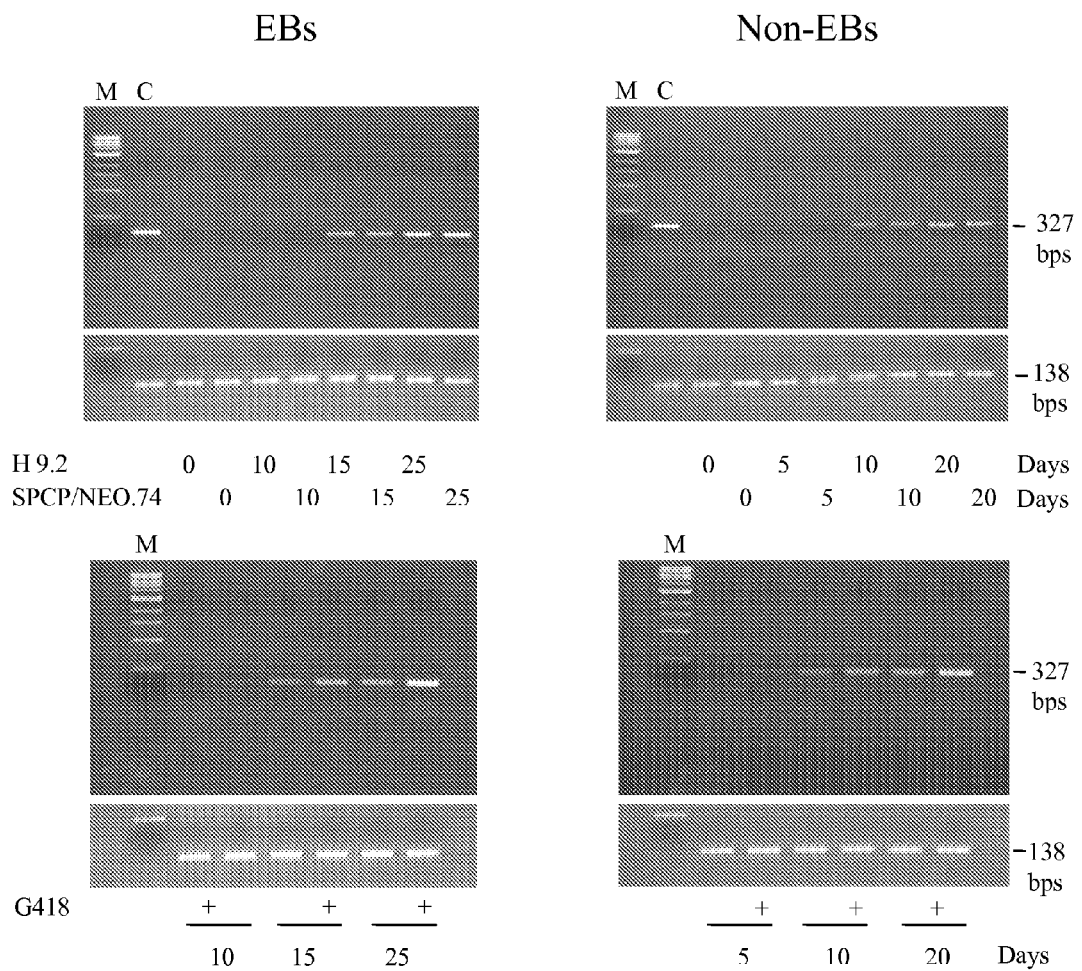
FIG. 2 shows relative RNA levels of surfactant protein C in G418 selected and nonselected differentiating hES cells. SPC specific RT-PCR was performed using total RNA isolated from differentiating cultures of hES cell lines, H9.2 and SPCP/NEO.74. Left panels (top and bottom) are data obtained from differentiating cells subjected to EB formation. Right panels (top and bottom) are data obtained from differentiating cells without EB formation. The two bottom panels show the results from G418 selected SPCP/NEO.74 hES cells. The far left lane of each panel is a 1 kb DNA ladder (marker). Lane 2 of the two top panels represents the SPC specific RT-PCR positive control using RNA isolated from the ATII cell line A549. The bottom section of all panels shows the 18S specific RT-PCR, demonstrating that changes in the amount of SPC specific 327-bp RT-PCR product was due to corresponding changes in SPC RNA expression. Total days of differentiation at which the RNA samples were obtained are indicated by D0 (day 0), D10 (day 10), D15 (day 15), D20 (day 20), and D25 (day 25).

The structure of the human SPC promoter-neomycin transgene (3'-hprt-SPCP.NEO) is depicted in FIG. 1. The hES cell line, H9.2, was transfected with the linearized transgene as described in the Methods, and a stable transfected hES clone (SPCP/NEO.74) expressing a single copy of the transgene was selected for further investigation. To induce spontaneous differentiation in vitro, H9.2 and SPCP/NEO.74 cell lines were cultured in 6-well extra low attachment plates for 5 days to form EBs. The presence of ATII cells in the differentiating cultures of both hES cell lines was determined by RT-PCR specific for SPC RNA. No SPC RNA was detected in the undifferentiated hES cells (day 0) or in the differentiating cultures on day 10. SPC RNA was detected in differentiating cultures of H9.2 and SPCP/NEO.74 hES cells by day 15, with significant increases of SPC RNA observed in both hES cultures on day 25 (FIG. 2, upper left panel). The ability of hES cells to directly differentiate into ATII cells in vitro without EB formation was examined by culturing the cells on MATRIGEL® coated plates in differentiation medium (DM). SPC RNA expression was detected as early as day 10 in both hES cell lines under these culture conditions (FIG. 2, upper right panel). Therefore, compared to cultures differentiated via EB formation, ATII cells appeared 5 days earlier in differentiating hES cells cultured on MATRIGEL® coated plates. To examine whether hES cell-derived ATII cells can be enriched by genetic selection, differentiating cultures of SPCP/NEO.74, with or without EB formation, were subjected to G418 treatment (20 g/ml). SPC RNA expression was detected in G418 selected cultures with EB formation on day 10 (FIG. 2, lower left panel) and without EB formation on day 5 (FIG. 2, lower right panel), but not in non-selected cultures at corresponding time points. In addition, significantly higher levels of SPC RNA in G418 selected cells were observed compared to non-selected cells at the longer time points of differentiation (FIG. 2, lower panels). Collectively, these results indicate that the SPCP/NEO.74 differentiating cell cultures can be enriched in ATII cells after selection with G418 treatment, and that hES cell-derived ATII cells can be generated efficiently on MATRIGEL® plates without EB formation.

Flow Cytometry Analysis of SPC Protein Expression.

Figure 3:
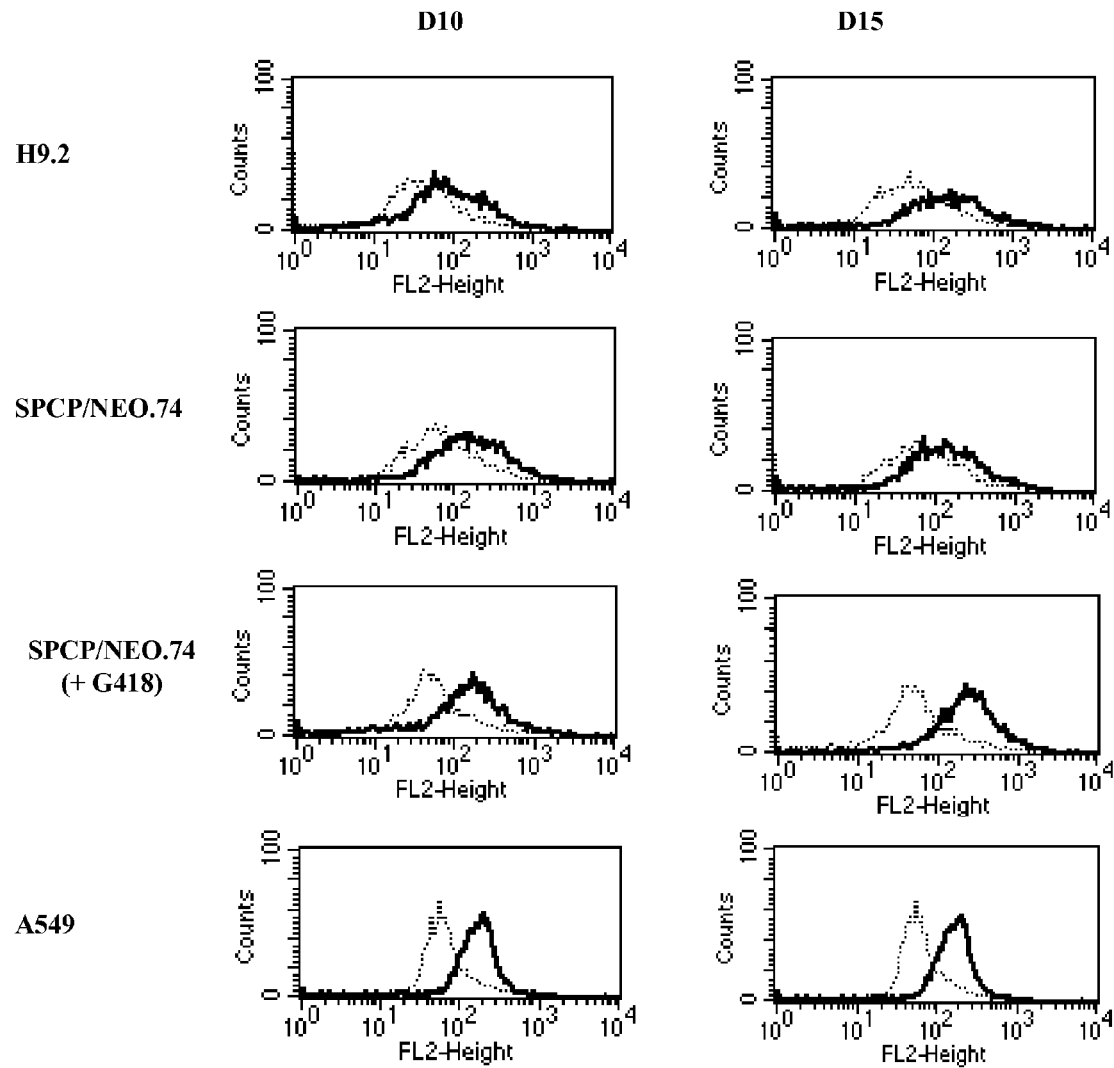
FIG. 3 shows the results of flow cytometry examining surfactant protein C expression in G418 selected and nonselected cultures of differentiating hES cells. Human ES cell lines, H9.2 and SPCP/NEO.74, were induced to differentiate by culturing on MATRIGEL® coated plates with DM for 10 days (left panels) or 15 days (right panels). The differentiated cells were dissociated and immuno-stained by rabbit anti-human SPC antibody for flow cytometry analysis as described in the Methods. Results using the SPC antibody are depicted by solid lines, and non-immune rabbit serum controls are illustrated by dashed lines.

The differentiated hES cell cultures without EB formation (days 10 and 15) were examined for alveolar epithelial type II specific SPC protein expression by flow cytometry. These studies revealed low level SPC protein expression in the differentiated culture of H9.2 cells on day 10, which did not increase on prolonged culture (15 days) (FIG. 3). Similar SPC protein levels were observed in the differentiated cultures of the SPCP/NEO.74 cell line. In contrast, when genetically selected by G418 treatment for 10 and 15 days, differentiated cultures of SPCP/NEO.74 exhibited significantly higher levels of SPC protein expression (FIG. 3). The levels of SPC protein in the genetically selected SPCP/NEO.74 cultures were comparable to that of the human alveolar type II cell line A549.

Immunofluorescent Staining of SPC, SPA and SPB in hES-ATII Cells.

Figure 4:
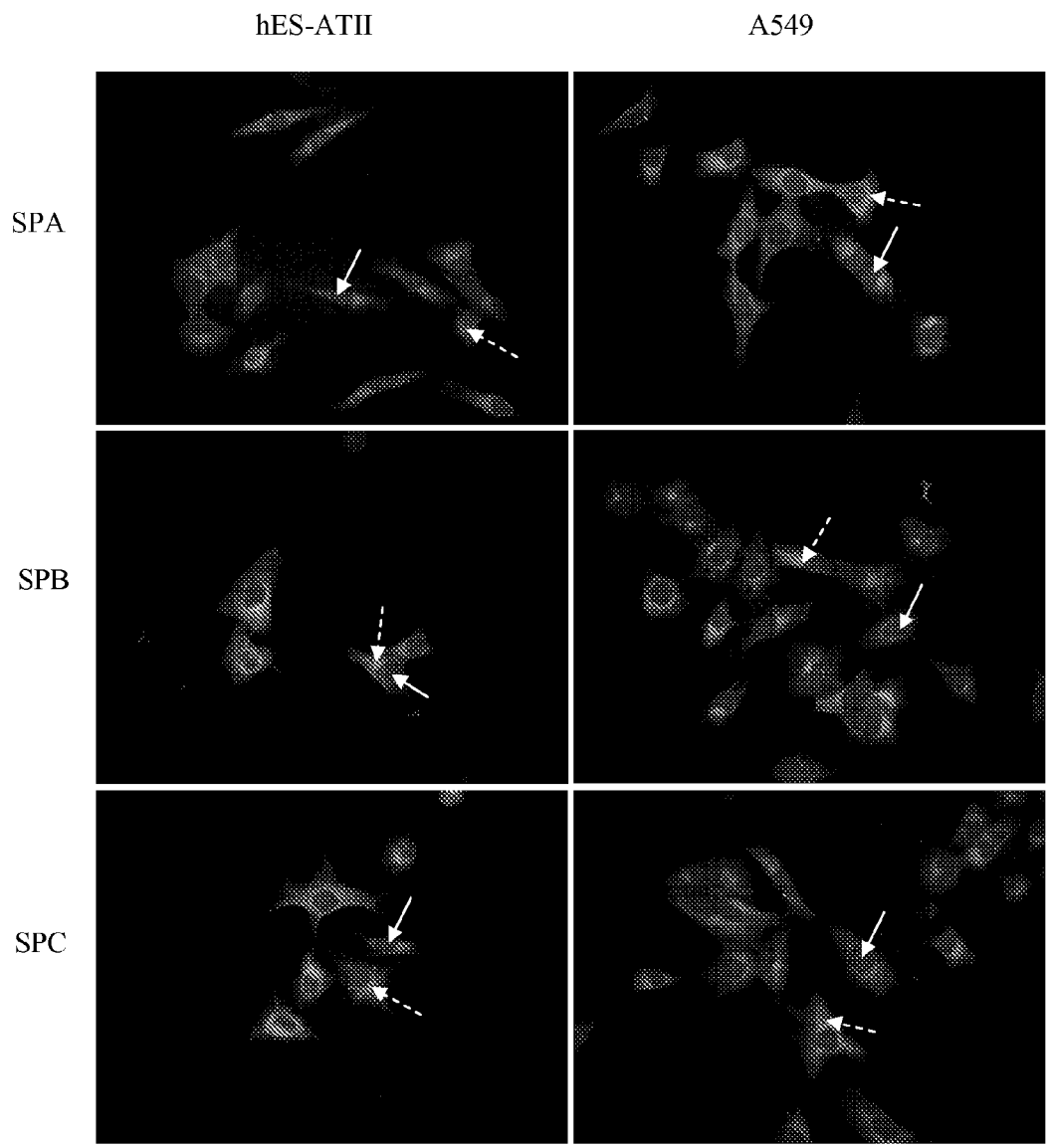
FIG. 4 is a set of photomicrographs showing immunofluorescence of surfactant proteins A, B, and C in SPCP/NEO.74 derived alveolar epithelial type II cells. The hES cell derived ATII cells generated by G418 selection from the SPCP/NEO.74 cell line and A549 cells were immunostained by rabbit anti-human SPA, SPB, and SPC antibodies (red=bright areas indicated by broken white arrow), and nuclear counterstained with DAPI (blue=dark areas indicated by solid white arrows). Pictures were all taken at 400× magnification.
Figure 7:
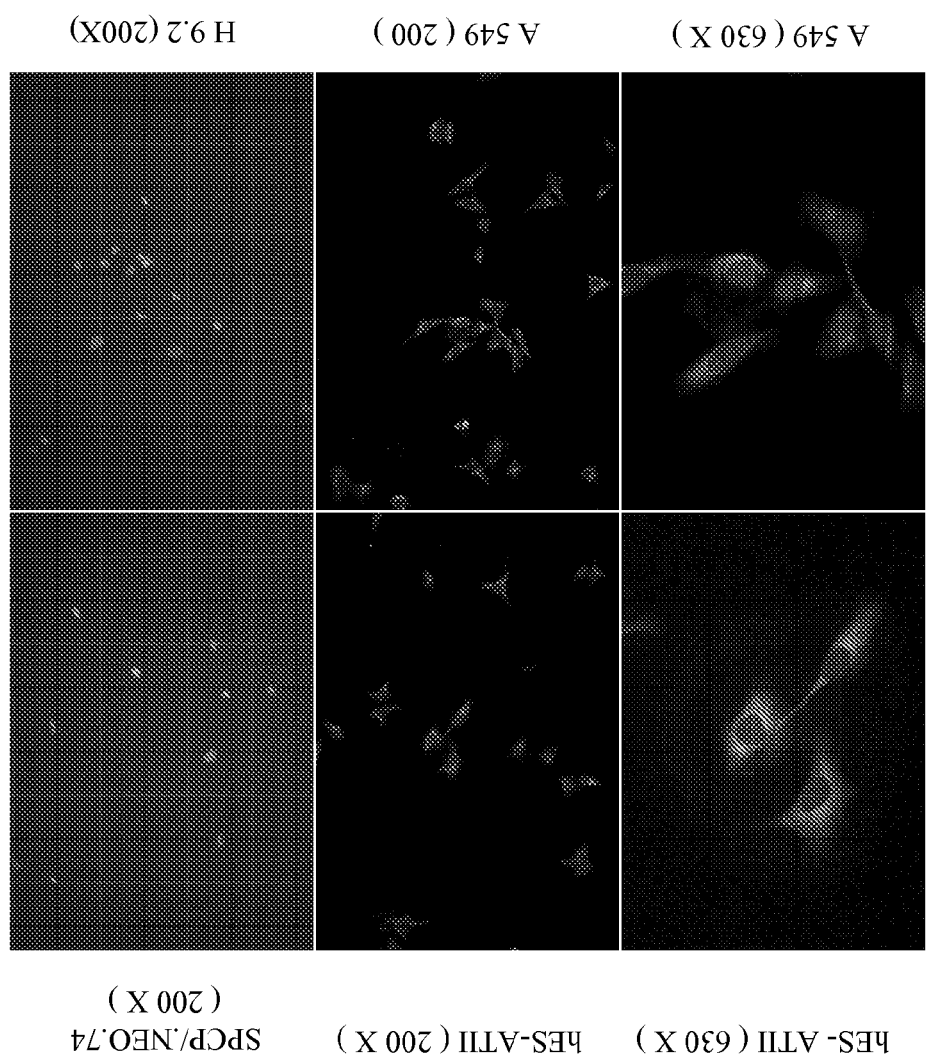
FIG. 7 is a group of photomicrographs showing that undifferentiated hES cells, H9.2 and SPCP/NEO.74 did not stain positive for SPC.

The synthesis of SPC is a unique feature of ATII cells and is commonly used to identify these cells from other lung parenchymal cells. Undifferentiated hES cells, H9.2 and SPCP/NEO.74, did not stain positive for SPC (FIG. 7). As expected, however, the G418 selected hES-ATII cells, as well as the A549 cells, displayed intense staining with rabbit anti-human SPC antibody (FIG. 4). At higher magnification (630×), SPC specific staining can be seen throughout the cytoplasm, with more intense staining observed in the perinuclear region, suggesting the presence of SPC in the Golgi/ER compartments (FIG. 7, bottom panels). In addition to SPC, the hES-ATII and A549 cells were shown to express surfactant proteins SPA and SPB by (FIG. 4).

Percentage of hES-ATII Cells in Differentiated Cell Cultures.

SPC staining was used to determine the percentage of ATII cells in differentiated hES cell cultures. SPC positive staining was displayed in only 11.2% of the differentiated hES cells in the non-selected H9.2 ES cell culture (Table 1). Similar results were observed in the non-selected SPCP/NEO.74 cell culture (12.6%). In stark contrast, 99.6% of cells in the G418 selected differentiated culture of SPCP/NEO.74 cells expressed SPC protein, indicating that G418 selection of the transfected hES cells produced an essentially pure culture of ATII cells.

TABLE 1

Relative ATII Cell Content in Nonselected and G418-selected Cultures of Differentiating hES Cells

| Cell | G418 selection | SPC-positive cells | SPC-negative cells | % of SPC-positive cells |
|---|---|---|---|---|
| H9.2 | − | 58 | 442 | 11.2 |
| SPC/NEO-HESC 74 | − | 63 | 437 | 12.6 |
| SPC/NEO-HESC 74 | + | 498 | 2 | 99.6 |

Identification of Lamellar Bodies in hES-ATII Cells by Transmission Electron Microscopy and Papanicolaous Staining.

Figure 5:
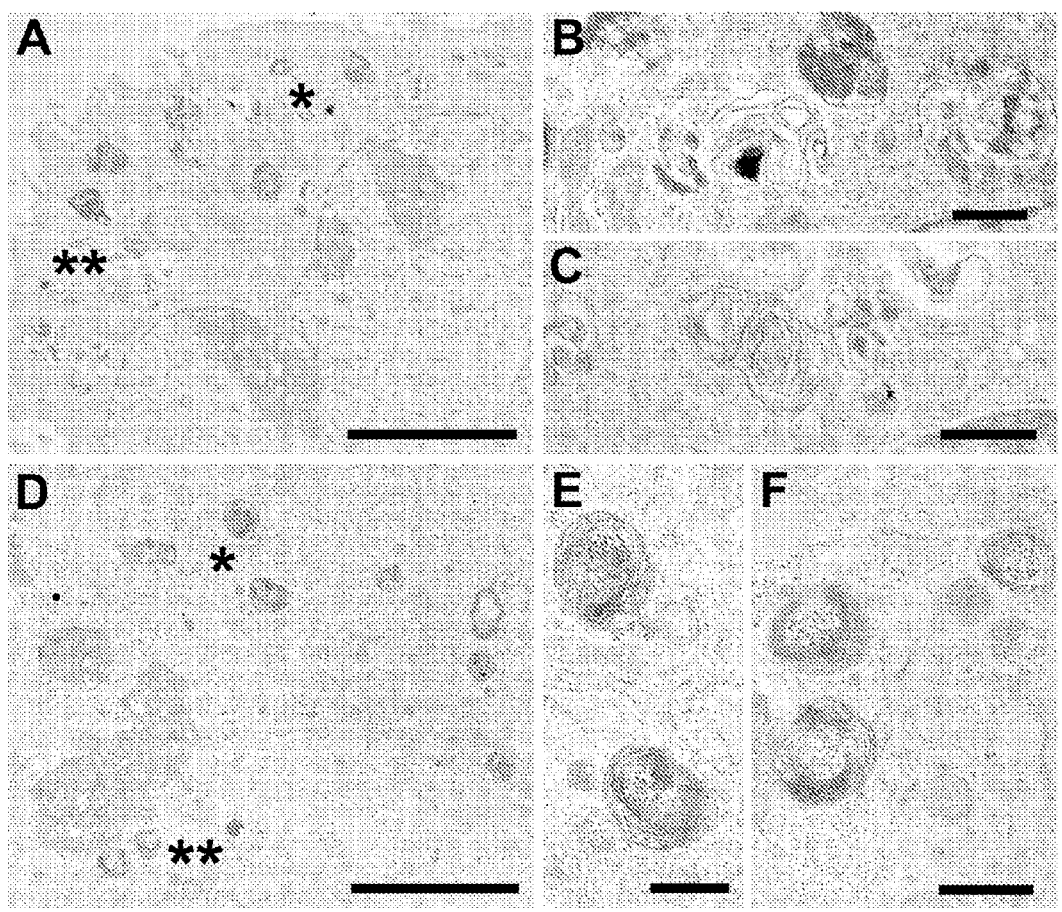
FIG. 5 is a group of transmission electron micrographs of A549 and hES-ATII cells. Panel A: A549 cells with characteristic cytoplasmic electron dense and loose lamellar bodies. Panels B and C: magnified views of regions (*) and (**), respectively, more clearly showing the structure of the lamellar bodies. Panel D: ES derived ATII cells showing similar lamellar bodies and other morphological characteristics as the A549 cells. Panels E and F: magnified views of regions (*) and (**) in panel D, respectively, showing clear lamellar structures. Bars=5 µm in A and D. Bars=0.5 µm in B, C, E and F.
Figure 8:
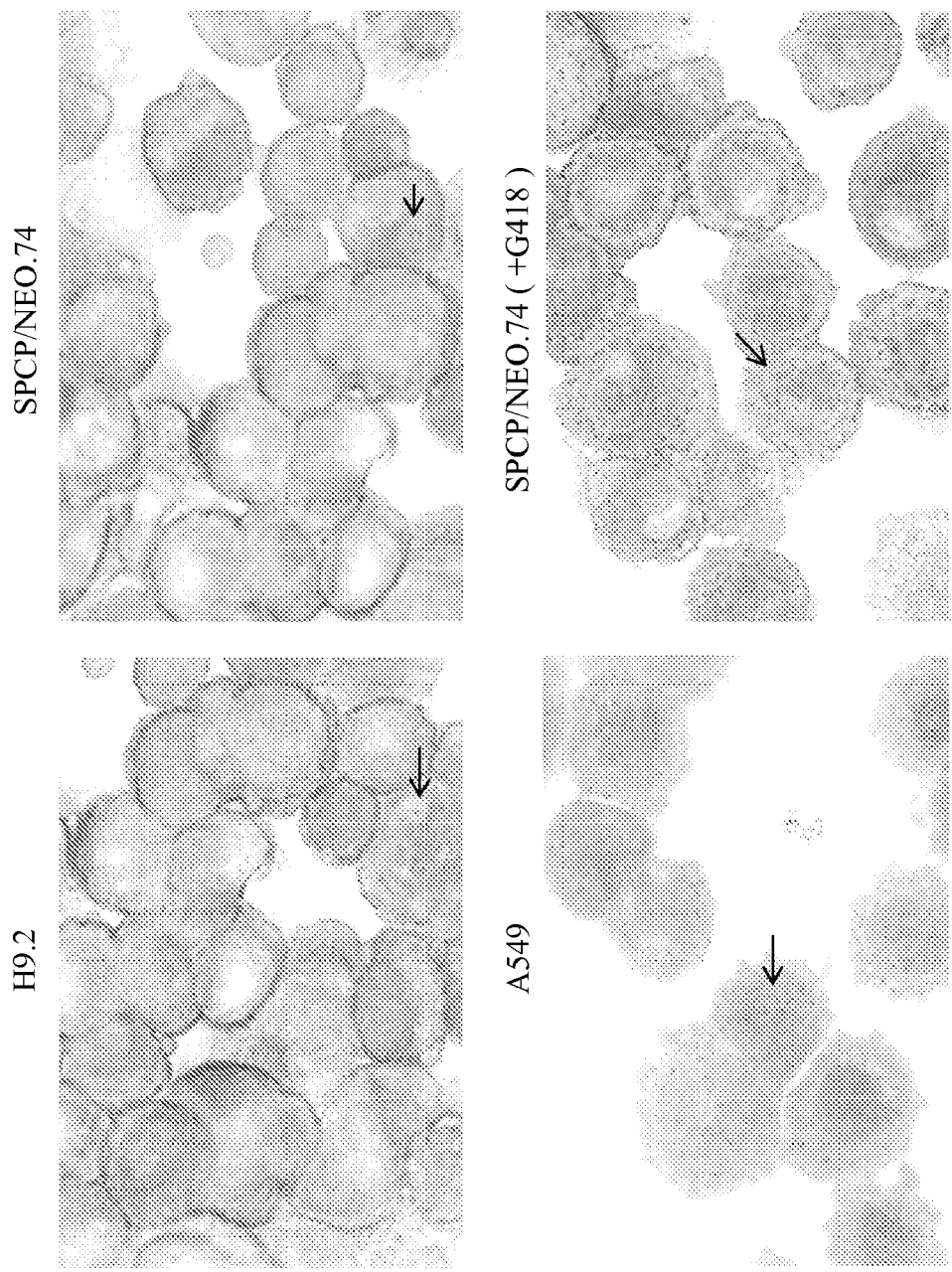
FIG. 8 is a photomicrograph showing lamellar bodies detected in the differentiated hES cultures by Papanicolaous staining.

Lamellar bodies are unusual intracellular organelles that contain pulmonary surfactant proteins and lipids. The presence of lamellar bodies is a criterion traditionally used for the identification of ATII cells. To determine if the hES-ATII cells contained these intracellular organelles, G418 selected hES-ATII cells were examined by transmission electron microscopy. The hES-ATII cells exhibited ultrastructural features characteristic of human type II cells, including cytoplasmic organelles with clear appearance of Lamellar bodies as seen in A549 cells (29) (FIG. 5). Supporting the electron microscopy data, lamellar bodies were also detected in the differentiated hES cultures by Papanicolaous staining (FIG. 8), which is another procedure routinely employed for the identification of lamellar bodies (30).

Expression of Human Cystic Fibrosis Transmembrane Conductance Regulator (CFTR), Alpha-1-Antitrypsin (α-1AT) and Complement Proteins C3 and C5.

Figure 6:
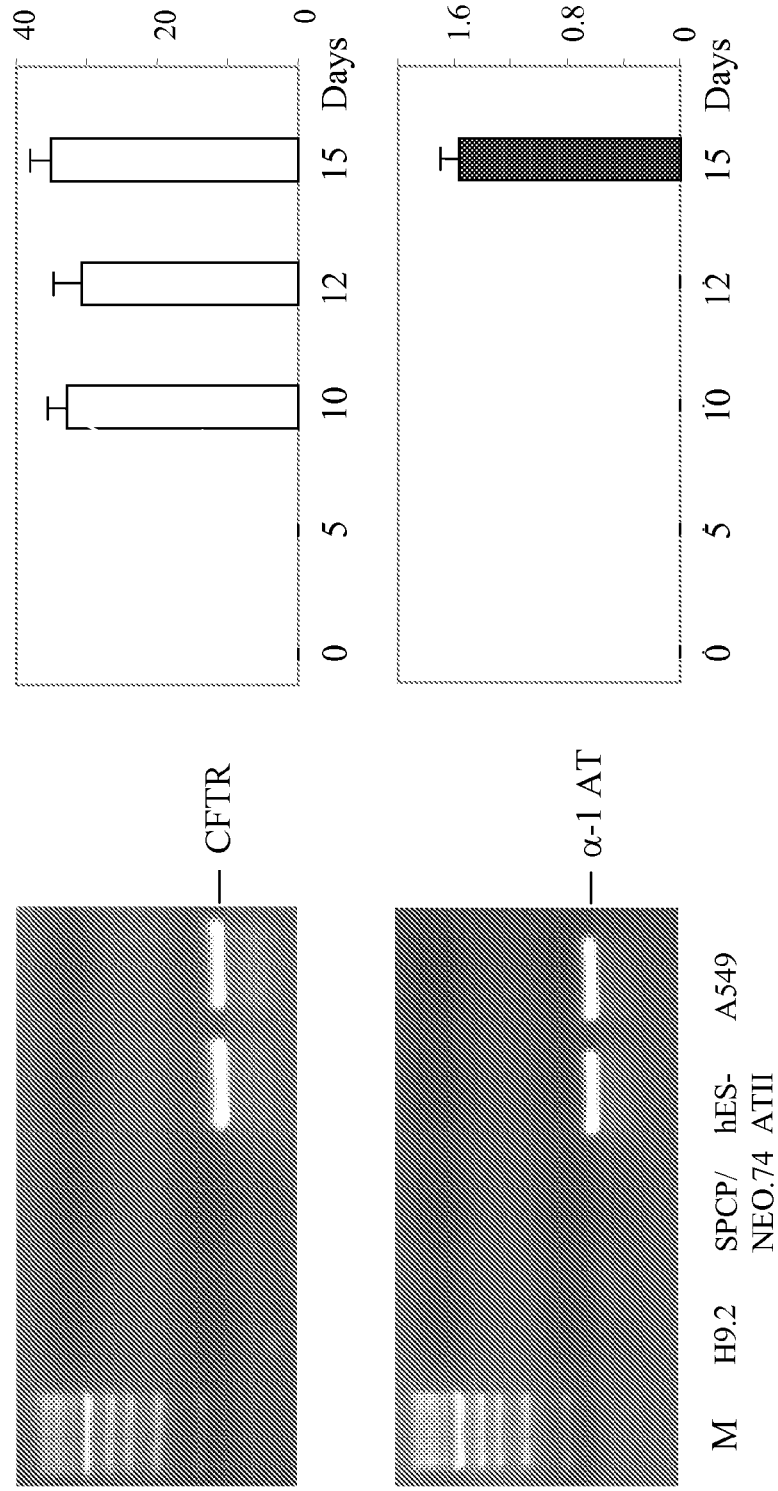
FIG. 6 shows the expression of CFTR, α-1 antitrypsin and the complement proteins C3 and C5 by hES-ATII cells. Total RNA isolated from hESC-derived ATII cells was used to examine CFTR and α-1AT expression by RT-PCR as described in the Methods. The RNA expression levels of CFTR and α-1AT in hES cell-derived ATII cells were comparable to that in A549 cells, but was not detectable in undifferentiated hES cell lines, H9.2 and SPCP/NEO.74 (left panels). C3 and C5 protein produced by hES derived ATII cells was determined by ELISA as described in the Methods. Upper right panel: bar graph depicting C3 protein levels from the hES cell-derived ATII cultures on days 10, 12, and 15. The numerical values on these days were 33±3, 32±3 and 35±3 ng/mg total protein/24 hr, respectively. Bottom right panel: bar graph depicting C5 protein levels from the hES cell-derived ATII cultures. C5 protein in the ES cell-derived ATII cells was measurable in the day 15 culture (1.6±0.1 ng/mg total protein/24 hr).

Because, ATII cells express CFTR and α-1AT in vivo and play an important role in alveolar homeostasis, the hES-ATII cells were examined for expression of CFTR and α-1AT RNA by RT-PCR. As anticipated, specific RNA transcripts of CFTR and α-1AT were observed in the hES-ATII cells and A549 cells, but not in the starting undifferentiated hES cell lines (FIG. 6). ATII cells are thought to be a major cell source of local production of complement proteins in the lung.

Therefore, it was also tested whether hES-ATII cells have the ability to synthesize and secrete C3 and C5, major components of the complement system with important diverse biological functions in inflammation, host defense, immunity, and tissue regeneration. ELISA measurements of the cell culture supernatants indicated that early differentiated ATII cells (day 10) synthesized and secreted C3 at a rate of 33±3 ng/mg/24 hr, which was comparable to that produced by the human alveolar type II cell line A549 (data not shown). Similar levels of C3 were also observed on day 12 and day 15 (FIG. 6, right upper panel). C5 was also detected but only in the day 15 cultures (1.6 ng/mg/24 hr) (FIG. 6, right lower panel). The amount of C5 produced by the hES-ATII cells was similar to the quantity of C5 produced by primary cultures of rat and human ATII cells (1).

Discussion

This is believed to be the first disclosure of a single step culture protocol that efficiently induces direct differentiation of hES cells to ATII cells without EB formation, and also the first description of a way to produce a highly pure population of ATII cells. Preferably the resulting cloned population of ATII phenotype cells is sufficiently pure (e.g. at least 99% ATII phenotype) to be suitable for implantation in a host lung tissue without significant risk of producing a teratoma. The hES differentiated ATII cells appear morphologically normal, express the characteristic surfactant proteins A, B, and C, CFTR and $\alpha$-1AT RNA as well as synthesize and secrete complement proteins C3 and C5. Thus, a unique approach is provided to reliably generate significant quantities of highly pure hES cell-derived ATII cells that will potentially be used in the future to reconstitute damaged lung alveolus as well as to treat genetic diseases that affect the lung.

The present single-culturing-step procedure and direct differentiation of ES cells into ATII cells contrasts with previous attempts at differentiation of ATII cells from hES cells, in which multiple steps were used to derive ATII cells from hES cells through EB formation. Previous approaches required prolonged time periods to develop the endoderm from which the ATII cells are derived, but in the end produced scarcely detectable ATII cells. Embodiments of the present methods which decrease the time and effort in generating hES derived ATII cells potentially facilitate their possible clinical use. As documented herein by RT-PCR, flow cytometric analysis, and immunostaining, hES cells cultured on matrix gel coated dishes, it is demonstrated that hES cells did in fact differentiate directly into ATII cells without embryonic body (EB) formation. In addition, SPC expression indicating the presence of ATII cells in the differentiating hES cell cultures occurred 5 days sooner in the absence of EB formation. Moreover, 11.2% of differentiated cells cultured on the matrix gel coated dishes were determined to express SPC protein on day 15 compared to 2.8% on day 33 when the EB formation approach was employed (31). It is proposed, in view of these collective results, that the components of matrix gel, such as laminin and collagen IV, may not only efficiently maintain the biological characteristics of ATII cells but also encourage differentiation of hES cells to ATII cells.

The use of ES cells as a source of transplantable cells in the lung alveolus will require the generation of significant quantities of highly pure ATII cells. To achieve this goal, genetic modification of hES cells was chosen so that the resulting differentiated ATII cells could be enriched through antibiotic selection. This approach was to establish a stable transfected hES cell line containing a single copy of the human SPC promoter-Neo fusion gene. When subjected to differentiation in vitro, it was hypothesized that ATII cells derived from this genetically modified hES cell line (SPCP/NEO.74) would express the Neo gene and would therefore survive G418 antibiotic selection, whereas, all the other differentiated cell lineages as well as the pluipotent cells would be eliminated by G418 selection. Immunocytochemical and flow cytometric analysis of the surviving G418 selected cells supported this hypothesis, indicating that this genetic selection approach resulted in an enrichment of hES-ATII cells to more than 99% when cultured on matrix gel coated plates. The above-described protocol reproducibly produced from each 10 cm culture dish more than $10^6$ essentially pure ATII cells within 15 days of differentiation, which will provide in a timely manner sufficient numbers of pure ATII cells for future transplantation investigations.

Ultrastructural examination by transmission electron microscopy and Papanicolaous staining demonstrated that the hES-ATII cells are morphologically normal and exhibit typical Lamellar bodies, which are a characteristic hallmark of primary ATII cells. The hES-ATII cells were shown to exhibit normal important biological functions, such as the synthesis of surfactant proteins A, B, and C. Moreover, these cells expressed RNA specific for CFTR and $\alpha$-1AT, suggesting that they may have therapeutic value in the treatment of patients with cystic fibrosis or $\alpha$-1AT deficiency. The hES-ATII cells also synthesized and secreted complement proteins C3 and C5, which are important in inflammation and host defense in the lung. Activation of C3 and C5 produces the potent complement anaphylatoxins, C3a and C5a. Recent reports indicate that C3a and C5a have novel and important roles in tissue regeneration (32), and neurogenesis (33). It is proposed in light of these findings that C3 and C5 synthesized and secreted by ATII cells are not only important in mediating pulmonary inflammation and host defense but could also play critical biological roles in alveolus regeneration and repair. In conclusion, this study provides the first description of a reliable single step procedure that can be employed to drive the differentiation of hES cells into a highly pure population of ATII cells, thereby providing a practical source of cells for repair of distal lung injury and for potential treatment of pulmonary genetic disorders.

Method of Preparing a Population of In Vitro Cultured Cells of A TII Cell Lineage Derived from Embryonic Stem Cell(s).

A population of in vitro cultured cells of alveolar epithelial type II (ATII) cell lineage derived from at least one embryonic stem cell includes: (a) Culturing at least one embryonic stem cell in vitro in a medium comprising MATRIGEL®, to produce differentiated cells without formation of an embryonic body. At least some of the differentiated cells are of ATII cell phenotype. (b) Identifying the differentiated cells of ATII cell phenotype by detecting expression of at least one biomarker of ATII cells. (c) Isolating the differentiated cells having ATII cell phenotype. In some cases, this may include selecting a purified population of differentiated cells wherein at least 99% of the cells have ATII cell phenotype. The method further includes (d) Cloning the isolated cells to produce a population of cells having ATII cell phenotype. Preferably this includes producing a population of more than $10^6$ cells within 15 days of differentiation, wherein at least 99% of the population have ATII phenotype.

In some instances the selected biomarker comprises surfactant protein C(SPC). In some instances the selected biomarker comprises cystic fibrosis transmembrane conductance receptor (CFTR). In some instances the selected biomarker comprises $\alpha$-1-antitrypsin $\alpha$-1 AT). In still other instances the selected biomarker comprises complement protein C3 or C5, or both.

An embryonic stem cell employed in the method may in some cases comprise a transgene operably linked to a cell-specific promoter. For example, the transgene may comprise a drug resistance gene that, when expressed, is capable of imparting resistance to the drug in the stem cell or progeny thereof.

Method of Repairing Injured or Diseased Alveolar Epithelial Tissue

An in vivo method of repairing injured or diseased alveolar epithelial tissue in the lung of a mammal includes transplanting into the lung, at a site comprising injured or diseased alveolar epithelial tissue, a population of differentiated embryonic stem cells, or progeny thereof, at least 99% of which have ATII phenotype, wherein the population of cells is prepared in accordance with the above-described method, and is effective to repair at least a portion of the injured or diseased alveolar epithelial tissue at the site. The differentiated embryonic stem cell, or progeny thereof, may comprise a transgene, which encodes a desirable gene product (e.g., a therapeutic protein or peptide), operably linked to a cell-specific promoter.

Method of Treating a Genetic Disease Affecting Alveolar epithelial Tissue

An in vivo method of treating a genetic disease affecting alveolar epithelial tissue in the lung of a mammal comprises transplanting into the lung, at a site comprising alveolar epithelial tissue detrimentally affected by the genetic disease, a population of differentiated embryonic stem cells, or progeny thereof, at least 99% of which have ATII phenotype. This population of cells is prepared as described above. The differentiated embryonic stem cell, or progeny thereof, comprises a transgene that encodes a gene product which ameliorates the genetic disease or its detrimental effects in the alveolar epithelial tissue at least at the site of implantation when expressed in vivo. An embryonic stem cell, or its progeny may comprise a transgene operably linked to a cell-specific promoter, wherein the transgene encodes a therapeutic gene product.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments of the invention have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

REFERENCES

The following references are cited in the foregoing description.

1. Strunk, R. C., Eidlen, D. M. & Mason, R. J. (1988) *J Clin Invest* 81, 1419-26.
2. Rothman, B. L., Despins, A. W. & Kreutzer, D. L. (1990) *J Immunol* 145, 592-8.
3. Zhao, Y. X., Andoh, A., Shimada, M., Takaya, H., Hata, K., Fujiyama, Y. & Bamda, T. (2000) *Int J Mol Med* 5, 415-9.
4. Mason, R. J. (2006) *Respirology* 11 Suppl, S 12-5.
5. Welsh, M. J., Ramsey, B. W., Accurso, F. J., Cutting, G. R. (2001) in *The Metabolic Basis of Inherited Disease*, ed. Scriver, C. R., Beaudet, A. L., Sly, W. S., Valle, D. (McGraw-Hill, New York), pp. 5121-5188.
6. Brochiero, E., Dagenais, A., Prive, A., Berthiaume, Y. & Grygorczyk, R. (2004) *Am J Physiol Lung Cell Mol Physiol* 287, L382-92.
7. Chroneos, Z. C., Wert, S. E., Livingston, J. L., Hasseft, D. J. & Whitsett, J. A. (2000) *J Immunol* 165, 3941-50.
8. Fang, X., Song, Y., Hirsch, J., Galiefta, L. J., Pedemonte, N., Zemans, R. L., Dolganov, G., Verkman, A. S. & Matthay, M. A. (2006) *Am J Physiol Lung Cell Mol Physiol* 290, L242-9.
9. Wang, G., Bunnell, B. A., Painter, R. G., Quiniones, B. C., Tom, S., Lanson, N. A., Jr., Spees, J. L., Bertucci, D., Peister, A., Weiss, D. J., Valentine, V. G., Prockop, D. J. & Kolls, J. K. (2005) *Proc Natl Acad Sci USA* 102, 186-91.
10. Swystun, V., Chen, L., Factor, P., Siroky, B., Bell, P. D. & Matalon, S. (2005) *Am J Physiol Lung Cell Mol Physiol* 288, L820-30.
11. Boutten, A., Venembre, P., Seta, N., Hamelin, J., Aubier, M., Durand, G. & Dehoux, M. S. (1998) *Am J Respir Cell Mol Biol* 18, 511-20.
12. Gadek, J. E., Fells, G. A., Zimmerman, R. L., Rennard, S. I. & Crystal, R. G. (1981) *J Clin Invest* 68, 889-98.
13. Wobus, A. M. (2001) *Mol Aspects Med* 22, 149-64.
14. Odorico, J. S., Kaufman, D. S. & Thomson, J. A. (2001) *Stem Cells* 19, 193-204.
15. Wobus, A. M., Wallukat, G. & Hescheler, J. (1991) *Differentiation* 48, 173-82.
16. Wobus, A. M., Kaomei, G., Shan, J., Wellner, M. C., Rohwedel, J., Ji, G., Fleischmann, B., Katus, H. A., Hescheler, J. & Franz, W. M. (1997) *J Mol Cell Cardiol* 29, 1525-39.
17. Muller, M., Fleischmann, B. K., Selbert, S., Ji, G. J., Endl, E., Middeler, G., Muller, O. J., Schlenke, P., Frese, S., Wobus, A. M., Hescheler, J., Katus, H. A. & Franz, W. M. (2000) *Faseb J* 14, 2540-8.
18. Okabe, S., Forsberg-Nilsson, K., Spiro, A. C., Segal, M. & McKay, R. D. (1996) *Mech Dev* 59, 89-102.
19. Brustle, O., Jones, K. N., Learish, R. D., Karram, K., Choudhary, K., Wiestler, O. D., Duncan, I. D. & McKay, R. D. (1999) *Science* 285, 754-6.
20. Kramer, J., Hegert, C., Guan, K., Wobus, A. M., Muller, P. K. & Rohwedel, J. (2000) *Mech Dev* 92, 193-205.
21. Buttery, L. D., Boume, S., Xynos, J. D., Wood, H., Hughes, F. J., Hughes, S. P., Episkopou, V. & Polak, J. M. (2001) *Tissue Eng* 7, 89-99.
22. Dani, C., Smith, A. G., Dessolin, S., Leroy, P., Staccini, L., Villageois, P., Darimont, C. & Ailhaud, G. (1997) *J Cell Sci* 110 (Pt 11), 1279-85.
23. Segev, H., Fishman, B., Ziskind, A., Shulman, M. & Itskovitz-Eldor, J. (2004) *Stem Cells* 22, 265-74.
24. Ali, N. N., Edgar, A. J., Samadikuchaksaraei, A., Timson, C. M., Romanska, H. M., Polak, J. M. & Bishop, A. E. (2002) *Tissue Eng* 8, 541-50.

25. Samadikuchaksaraei, A., Cohen, S., Isaac, K., Rippon, H. J., Polak, J. M., Bielby, R. C. & Bishop, A. E. (2006) *Tissue Eng* 12, 867-75.
26. Van Vranken, B. E., Romanska, H. M., Polak, J. M., Rippon, H. J., Shannon, J. M. & Bishop, A. E. (2005) *Tissue Eng* 11, 1177-87.
27. Rippon, H. J., Polak, J. M., Qin, M. & Bishop, A. E. (2006) *Stem Cells* 24, 1389-98.
28. Klug, M. G., Soonpaa, M. H., Koh, G. Y. & Field, L. J. (1996) *J Clin Invest* 98, 216-24.
29. Stearns, R. C., Paulauskis, J. D. & Godleski, J. J. (2001) *Am J Respir Cell Mol Biol* 24, 108-15.
30. Dobbs, L. G. (1990) *Am J Physiol* 258, L134-47.
31. Samadikuchaksaraei, A. & Bishop, A. E. (2006) *Methods Mol Biol* 330, 233-48.
32. Markiewski, M. M., Mastellos, D., Tudoran, R., DeAngelis, R. A., Strey, C. W., Franchini, S., Wetsel, R. A., Erdei, A. & Lambris, J. D. (2004) *J Immunol* 173, 747-54.
33. Rahpeymai, Y., Hietala, M. A., Wilhelmsson, U., Fotheringham, A., Davies, I., Nilsson, A. K., Zwimer, J., Wetsel, R. A., Gerard, C., Pekny, M. & Pekna, M. (2006) *Embo J* 25, 1364-74.
34. Gou, D., Narasaraju, T., Chintagari, N. R., Jin, N., Wang, P. & Liu, L. (2004) *Nucleic Acids Res* 32, e134.
35. Zheng, B., Mills, A. A. & Bradley, A. (1999) *Nucleic Acids Res* 27, 2354-60.
36. Xu, C., Inokuma, M. S., Denham, J., Golds, K., Kundu, P., Gold, J. D. & Carpenter, M. K. (2001) *Nat Biotechnol* 19, 971-4.

What is claimed is:

1. A method of preparing a population of in vitro cultured cells of alveolar epithelial type II (ATII) cell lineage derived from at least one embryonic stem cell, comprising;
   (a) culturing said at least one embryonic stem cell, wherein said at least one embryonic stem cell comprises a transgene operably linked to a cell-specific promoter, in vitro in a medium comprising MATRIGEL® (a gelatinous protein mixture secreted by Engelbreth-Holm-Swarm (EHS) mouse sarcoma cells), to produce differentiated cells without formation of an embryonic body, wherein at least some 99% of said differentiated cells are of ATII cell phenotype;
   (b) identifying said differentiated cells of ATII cell phenotype by detecting expression of at least one biomarker of ATII cells;
   (c) isolating the differentiated cells having ATII cell phenotype; and
   (d) cloning the isolated cells to produce a population of cells having ATII cell phenotype.

2. The method of claim 1 wherein said at least one biomarker comprises surfactant protein C.

3. The method of claim 1 wherein said at least one biomarker comprises cystic fibrosis transmembrane conductance receptor.

4. The method of claim 1 wherein said at least one biomarker comprises α-1-antitrypsin.

5. The method of claim 1 wherein said at least one biomarker comprises complement protein C3 or C5, or both.

6. The method of claim 1 wherein said transgene comprises a drug resistance gene that, when expressed, is capable of imparting resistance to said drug in said stem cell or progeny thereof.

7. The method of claim 1 wherein in (c), isolating the differentiated cells having the ATII cell phenotype comprises selecting a purified population of differentiated cells wherein at least 99% of the cells have ATII cell phenotype.

8. The method of claim 1 wherein in (d), cloning the isolated cells to produce a population of cells having ATII cell phenotype comprises producing a population of more than $10^6$ cells within 15 days of differentiation, wherein at least 99% of said population have ATII phenotype.

9. An in vivo method of repairing injured or diseased alveolar epithelial tissue in the lung of a mammal, comprising transplanting into said lung, at a site comprising injured or diseased alveolar epithelial tissue, a population of differentiated embryonic stem cells, or progeny thereof, at least 99% of which have ATII phenotype, wherein said population of cells is prepared in accordance with the method of claim 1, and is effective to repair at least a portion of said injured or diseased alveolar epithelial tissue at said site.

10. The method of claim 9 wherein said at least one said differentiated embryonic stem cell, or progeny thereof, comprises a transgene operably linked to a cell-specific promoter, wherein said transgene encodes a therapeutic gene product.

11. An in vivo method of treating a genetic disease affecting alveolar epithelial tissue in the lung of a mammal, comprising transplanting into said lung, at a site comprising alveolar epithelial tissue detrimentally affected by said genetic disease, a population of differentiated embryonic stem cells, or progeny thereof, at least 99% of which have ATII phenotype, wherein said population of cells is prepared in accordance with the method of claim 1, and said transgene encodes a gene product that ameliorates the detrimental effects of said genetic disease in said alveolar epithelial tissue.

12. The method of claim 11 wherein said at least one differentiated embryonic stem cell, or progeny thereof, comprises a transgene operably linked to a cell-specific promoter, wherein said transgene encodes a therapeutic gene product.

13. The method of claim 6, wherein the transgene is a human SPC promoter-Neo$^r$ fusion gene.

14. The method of claim 13, wherein said culturing further comprises adding about 20 μg/ml of G418 to said medium on about day 6 of culturing.

15. The method of claim 6, wherein the transgene encodes a therapeutic product.

* * * * *